United States Patent
Raoult et al.

(10) Patent No.: US 11,091,735 B2
(45) Date of Patent: Aug. 17, 2021

(54) POLYVALENT CULTURE MEDIUM FOR ANAEROBIC BACTERIA UNDER AEROBIC CONDITIONS

(71) Applicants: FONDATION MEDITERRANEE INFECTION, Marseilles (FR); UNIVERSITE D'AIX MARSEILLE, Marseilles (FR); ASSISTANCE PUBLIQUE—HOPITAUX DE MARSEILLE, Marseilles (FR); CENTRE NATIONAL DE LA RECHERCHE SCIENTIFIQUE (CNRS), Paris (FR); INSERM (INSTITUT NATIONAL DE LA SANTE ET DE LA RECHERCHE MEDICALE), Paris (FR)

(72) Inventors: Didier Raoult, Marseilles (FR); Saber Khelaifia, Marseilles (FR); Marion Bonnet, Marseilles (FR)

(73) Assignees: FONDATION MEDITERRANEE INFECTION FACULTÉ DE MÉDECINE, Marseilles (FR); UNIVERSITE D'AIX MARSEILLE, Marseilles (FR); ASSISTANCE PUBLIQUE—HOPITAUX DE MARSEILLE, Marseilles (FR); CENTRE NATIONAL DE LA RECHERCHE SCIENTIFIQUE (CNRS), Paris (FR); INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 39 days.

(21) Appl. No.: 16/636,014

(22) PCT Filed: Aug. 1, 2018

(86) PCT No.: PCT/FR2018/051987
§ 371 (c)(1),
(2) Date: Feb. 2, 2020

(87) PCT Pub. No.: WO2019/030446
PCT Pub. Date: Feb. 14, 2019

(65) Prior Publication Data
US 2020/0157490 A1    May 21, 2020

(30) Foreign Application Priority Data

Aug. 8, 2017    (FR) .................................... 1757574

(51) Int. Cl.
C12N 5/00    (2006.01)
C12N 1/20    (2006.01)

(52) U.S. Cl.
CPC .................................. *C12N 1/20* (2013.01)

(58) Field of Classification Search
CPC ....................................................... C12N 1/20
See application file for complete search history.

(56) References Cited

FOREIGN PATENT DOCUMENTS

WO    2014/064359 A1    5/2014
WO    2015/162377 A1    10/2015

OTHER PUBLICATIONS

ISR_for_International_Application_PCTFR2018/051987, Dec. 19, 2018.
Written Opinion_for_International_Application_PCTFR2018/051987, dated Dec. 19, 2018.
N. Dione et al.: "A quasi-universal medium to break the aerobic/anaerobic bacterial culture dichotomy in clinical microbiology", Clinical Microbiology and Infection., vol. 22, No. 1, Jan. 1, 2016 (Jan. 1, 2016), p. 53-58, XP05055361668 DOI: 10.1016/j.cmi.2015.10.032 ISSN:1198-743X.
S. Khelaifia et at.:"Aerobic culture of methanogenic Archaea Without an External Source of Hydrogen", Mar. 24, 2016 (Mar. 24, 2016), vol. 35, No. 6, p. 985-991, XP035893122 DOI: 10.1007/S10096-016-2627-7 ISSN:0934-9723.
WO 2014/064359 A1—Espacenet English Translation, May 1, 2014.
WO 2015/162377 A1—Espacenet English Translation, Oct. 29, 2015.

*Primary Examiner* — Albert M Navarro
(74) *Attorney, Agent, or Firm* — Ladas & Parry LLP; Malcolm J. MacDonald

(57) ABSTRACT

The present invention relates to a polyvalent culture medium for anaerobic bacteria under aerobic conditions in blood culture bottles.
The present invention provides a polyvalent culture medium for culture in aerobic atmosphere of anaerobic bacteria or aerobic bacteria comprising a basal culture medium for bacteria characterized in that it further comprises a mixture of the following antioxidant compounds: sodium hydrosulphide ($Na_2S$), L-cysteine, ascorbic acid, glutathione, catalase, ubiquinol and lipoic acid.

15 Claims, 1 Drawing Sheet

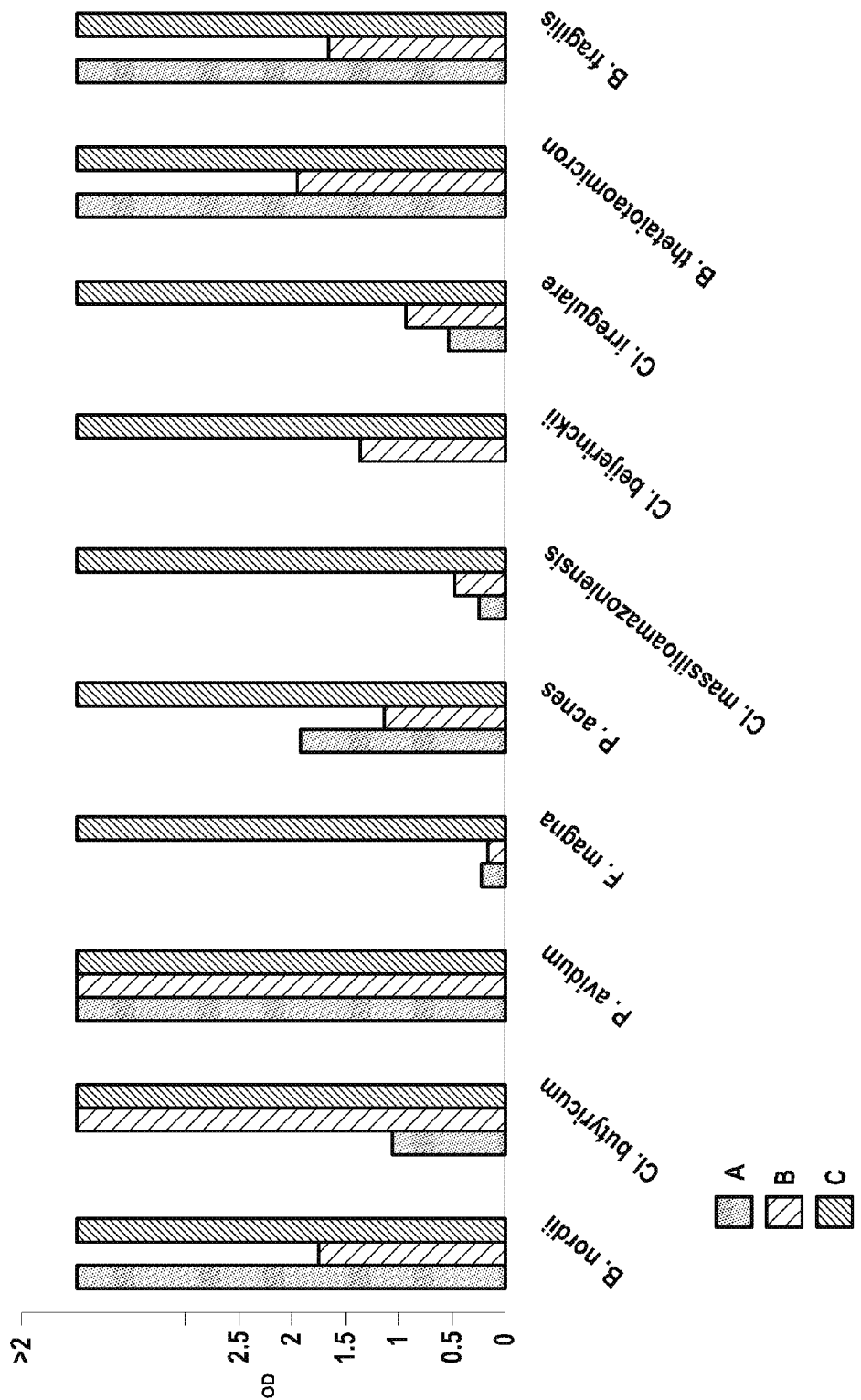

POLYVALENT CULTURE MEDIUM FOR ANAEROBIC BACTERIA UNDER AEROBIC CONDITIONS

The present invention relates to a polyvalent culture medium for anaerobic bacteria under aerobic conditions in blood culture bottles.

Anaerobic bacteria are oxygen-sensitive bacteria. There are strict anaerobic bacteria (extremely sensitive to oxygen), which must never be in contact with oxygen in order to grow, and aerotolerant anaerobic bacteria, which can be exposed to a low concentration of oxygen without inhibiting their growth. This sensitivity to oxygen is related to the fact that these bacteria lack enzyme systems. The latter normally allow the detoxification of reactive oxygen species; the absence of this detoxification leads to a toxic action of oxygen on these bacteria. To allow the growth of these strict anaerobic or aerotolerant anaerobic bacteria, "oxygen-free" culture processes have been implemented [1].

Shortening the time to diagnosis of bacteraemia remains a major challenge for microbiologists. Reliability and speed of diagnosis are key elements for improved patient management. In this respect, despite the commercialization of many molecular systems, culture in liquid culture media remains to date the optimal standard in the diagnosis of bacteraemia in clinical samples of fluid or body secretions such as stool, sputum, vaginal secretion samples, or blood samples. It is based on the incubation of two bottles containing it, for anaerobic and aerobic bacteria respectively in automated culture systems detecting bacterial growth.

Currently, hospital diagnosis of anaerobic bacteria is most commonly performed in liquid culture bottles containing an anaerobic atmosphere, i.e. an atmosphere that does not contain oxygen, where atmospheric oxygen is replaced by nitrogen, using a degassing process. Anaerobic and aerobic bacteria are grown in different culture bottles, i.e. two bottles, anaerobic and aerobic, are incubated in automated culture systems that detect bacterial growth.

In order to minimize the number of bottles to be taken to diagnose bacteraemia or to grow bacteria for research purposes, the inventors sought to provide a liquid culture medium that would allow both aerobic and anaerobic bacteria to grow in aerobic atmosphere.

It has recently been reported that strictly anaerobic bacterial species have been shown to grow in aerobic atmosphere using a basal culture medium supplemented with antioxidant compounds [2].

In WO2014/064359 and WO2015/162377, culture media enriched with antioxidant agents, namely uric acid, ascorbic acid, glutathione and sodium hydrosulphide were described to improve and facilitate the conditions for growth in acellular culture of strict anaerobic bacteria or bacteria whose growth is sensitive to oxygen tension and notably bacteria which are poorly tolerant of high oxygen tensions and for which optimal growth of the said bacteria requires an incubation atmosphere with a relatively low oxygen content compared with the oxygen content of the air. The best results described in WO 2015/162377 involved culture media supplemented with a mixture of antioxidants including uric acid.

After testing culture media supplemented with antioxidant compounds described in WO2014/064359 and WO2015/162377 in liquid form for blood culture, the inventors noticed that certain anaerobic bacteria, including some of the most commonly found bacteria in hospital practices, did not grow aerobically, namely *Bacteroides fragilis*, *Bacteroides nordii*, *Bacteroides thetaiotaomicron*, *Clostridium beijeirinckii*, *Clostridium butyricum*, *Clostridium massilioamazoniensis*, *Clostridium irregulare*, *Finegoldia magna*, *Propionibacterium acnes* and *Propionibacterium avidum*.

Based on the mixtures of antioxidant compounds described above, the best mixture appeared to be the combination of sodium hydrosulphide ($Na_2S$), L-cysteine, ascorbic acid, uric acid and glutathione. However, the culture media for anaerobic bacteria supplemented with this mixture of antioxidant compounds did not allow the growth of the hard-to-grow anaerobic bacteria described above.

In addition, according to the present invention, the inventors have sought a novel polyvalent liquid culture medium for culturing aerobic and anaerobic bacteria in aerobic atmosphere in the absence of uric acid since the latter has reduced dilution properties resulting in dissolution rates in aqueous solution which are not quantitatively reproducible from sample to sample.

According to the present invention, the inventors have therefore sought a novel polyvalent liquid culture medium for culturing aerobic and anaerobic bacteria in aerobic atmosphere in the absence of uric acid and further having improved growth properties notably with respect to the fastidious anaerobic bacteria commonly encountered such as *Bacteroides fragilis*, *Bacteroides nordii*, *Bacteroides thetaiotaomicron*, *Clostridium beijeirinckii*, *Clostridium butyricum*, *Clostridium massilioamazoniensis*, *Clostridium irregulare*, *Finegoldia magna*, *Propionibacterium acnes* and *Propionibacterium avidum*.

For this purpose, the inventors have tested a large number of combinations of various antioxidant compounds reported below (see Table 2) which have made it possible to define in a surprising manner a liquid culture medium supplemented with antioxidant compounds having improved growth properties for anaerobic bacteria under aerobic conditions compared with the combination of sodium hydrosulphide ($Na_2S$), L-cysteine, ascorbic acid and glutathione with or without uric acid, namely the mixture of the following 7 antioxidant compounds: sodium hydrosulphide ($Na_2S$), L-cysteine, ascorbic acid, glutathione, and three additional antioxidants, namely catalase, ubiquinol and lipoic acid. These media were tested for the cultivation of the 13 fastidious anaerobic bacteria including the anaerobic bacteria cited above and 20 aerobic bacteria most commonly encountered in hospital routine described below.

The present invention provides a polyvalent liquid culture medium for culture in aerobic atmosphere of anaerobic bacteria or aerobic bacteria comprising a basal culture medium for aerobic and anaerobic bacteria characterized in that it further comprises the mixture of the following antioxidant compounds: sodium hydrosulphide ($Na_2S$), L-cysteine, ascorbic acid, glutathione, catalase, ubiquinol and lipoic acid.

More particularly, the culture medium according to the invention comprises said antioxidant compounds in the following quantities and weight proportions per 1 L:

Sodium hydrosulphide: at least 0.25 g (0.025%), preferably from 0.25 g to 0.5 g (0.025 to 0.05%)

L-Cysteine: at least 0.25 g (0.025%), preferably 0.25 g to 0.5 g (0.025 to 0.05%)

Ascorbic acid: at least 0.5 g (0.05%), preferably from 0.5 to 1 g (0.05 to 0.1%)

Glutathione: at least 0.1 g (0.01%), preferably from 0.1 to 0.5 g (0.01 to 0.05%)

Catalase: at least 0.06 g (0.006%), preferably 0.06 to 0.16 g (0.006 to 0.016%)

Ubiquinol: at least 0.06 g (0.006%), preferably 0.06 to 0.16 g (0.006 to 0.016%)

Lipoic acid: at least 0.01 g (0.001%), preferably from 0.01 to 0.015 g (0.001 to 0.0015%)

More particularly still, the culture medium according to the invention comprises the following nutrient components in said basal culture medium:
- several sources of carbon and nitrogen, preferably selected from a yeast extract, an acetate salt and a tryptic peptone,
- a source of phosphorus, preferably a phosphate salt,
- at least one sugar, and
- at least one salt of metals selected from K, Mg, Na and Ca, preferably NaCl, as well as
- at least one pH-regulating buffer substance for adjusting the pH from 7 to 8, preferably $K_2HPO_4$ or $NaHCO_3$ for adjusting the pH to 7.5, and
- at least one vitamin or growth factor.

More particularly still, said basal culture medium is a conventional acellular bacterial medium comprising nutrient components selected from an extract of ground or lysed multicellular tissue, an enzyme digestate, notably an enzyme digestate of casein, soybean and/or animal tissue, a peptone, a yeast extract, a sugar such as dextrose or glucose, a NaCl and/or $Na_2PO_4$ salt.

More particularly still, said basal culture medium is a cell-free medium selected from an axenic medium consisting of chemical or biological substances defined qualitatively and quantitatively, and a cell-free medium comprising an extract of multicellular tissue grind or lysate.

More particularly still, said culture medium is a conventional acellular medium for anaerobic bacteria, notably a medium comprising components selected from an extract of ground material or lysate of multicellular tissue, an enzymatic digestate, notably an enzymatic digestate of casein, soya and/or of animal tissue, a peptone, a yeast extract, a sugar such as dextrose or glucose, a NaCl and/or $Na_2PO_4$ salt.

More particularly still, said basal culture medium is a conventional medium for the cultivation of anaerobic bacteria such as brain heart infusion, 5% sheep blood Columbia media or Schaedler medium as described below. Other suitable conventional media are *Brucella* or Wilkins-Chalgren media. Such acellular culture media are well known to the person skilled in the art.

In particular, polyvalent culture media for anaerobic microorganisms, especially Schaedler medium, can be used, said medium being supplemented with hydrocarbon compounds, preferably starch and sugar(s), and with said antioxidant compound(s).

More particularly still, said basal culture medium is a liquid culture medium for culturing anaerobic bacteria in a blood, stool, sputum or vaginal secretion sample.

More particularly still, said basal culture medium comprises the following nutrient components:
- Casein hydrolysate;
- Proteose peptone;
- Yeast extract;
- Sodium chloride (NaCl); and
- Glucose, and
- a growth factor: α-ketoglutarate.

More particularly still, said basal culture medium comprises the following components in the following quantities and weight proportions per 1 L:
- Casein hydrolysate: 15 g (1.5%)
- Proteose peptone: 15 g (1.5%)
- Yeast extract: 10 g (1%)
- α-Ketoglutarate: 2 g (0.2%)
- Sodium chloride (NaCl): 5 g (0.5%)
- Glucose: 10 g (1%)
- Dipotassium phosphate ($K2HPO_4$): 0.83 g (0.083%)
- Sodium hydrosulphide ($Na_2S$): 0.5 g (0.05%)
- L-Cysteine: 0.5 g (0.05%)
- Ascorbic acid: 1 g (0.1%)
- Glutathione: 0.1 g (0.01%)
- Catalase: 0.16 g (0.016%)
- Ubiquinol: 0.16 g (0.016%)
- Lipoic acid: 0.010 g (0.001%)

The pH of the solution is adjusted to 7.5±0.2 with 10 M KOH.

The present invention also relates to a process for the in vitro culture of an aerobic or anaerobic bacterium under aerobic atmosphere with a culture medium according to the invention.

More particularly, a said bacterium is cultured in a blood, stool, sputum or vaginal secretion sample.

More particularly still, a said fastidious strict anaerobic bacterium selected from *Akkermansia muciniphila, Bacteroides fragilis, Bacteroides nordii, Bacteroides thetaiotaomicron, Clostridium beijeirinckii, Clostridium butyricum, Clostridium massilioamazoniensis, Clostridium irregulare, Finegoldia magna, Propionibacterium acnes* and *Propionibacterium avidum, Prevotella denticola* and *Prevotella histicola* is cultured.

More generally, the medium according to the present invention also allows the cultivation of bacteria whose growth is sensitive to oxygen tension and notably bacteria which are poorly tolerant of high oxygen tensions and for which optimal growth of said bacteria requires an incubation atmosphere with an oxygen content relatively reduced in comparison with the oxygen content of the air in the absence of a specific culture medium such as a medium according to the present invention. It is therefore possible to distinguish among oxygen-sensitive bacteria:
- microaerophilic bacteria, meaning that they are not capable of growing in an atmosphere with an ambient oxygen concentration of about 21%, notably between 1% and 20%, most commonly about 2-2.5%, and
- strict anaerobic bacteria, meaning that they are not capable of growing in the presence of oxygen or in concentrations below microaerophilic concentrations, notably strictly below 1%, most commonly below 0.1%, ideally 0%. In order to culture strict anaerobic bacteria, in the absence of a specific culture medium such as a medium according to the present invention, they must either be cultured in oxygen-free incubators or in tubes which have been deoxygenated and they then grow only at the bottom of the tube.

Among the strict anaerobic bacteria, particular mention may be made of extracellular bacteria, i.e. bacteria that can only live outside cells.

Among the bacteria that can be cultured in microaerophilic atmosphere, it is possible to distinguish more particularly, intracellular bacteria, but also extracellular bacteria. As used here, "intracellular bacterium" means a bacterium that has the ability to multiply within a host cell. Intracellular bacteria, having the ability to grow under certain conditions in acellular media, are referred to as "facultative intracellular bacteria".

As used herein:
"facultative intracellular bacterium" means a bacterium that has the ability to multiply within a host cell in a cell-free environment, and "extracellular bacterium" means a bacterium that does not have the ability to multiply within a host cell and grows exclusively in a cell-free environment.

As used herein, "acellular culture medium" means a culture medium which does not include whole cells, including whole host cells in which said bacterium can multiply, when said bacterium is intracellular or facultatively intracellular. It is understood that whole cells must be alive to allow the bacterium to multiply within them.

More particularly, the present invention relates to the cultivation of anaerobic bacteria and the cultivation of intracellular microaerophilic bacteria.

More particularly still, said bacteria can be cultivated in a said incubation atmosphere comprising a molar proportion of oxygen greater than the maximum tolerated tension in the absence of antioxidant compounds for the same level of growth in the same culture period.

In practice, more particularly still, said bacterium can be cultivated in a so-called incubation atmosphere comprising a molar proportion of oxygen greater than 2.5% and less than or equal to 20%.

Advantageously, however, said bacteria according to the present invention are cultivated in an atmosphere comprising an oxygen content of more than 5%, notably in air containing 5% $CO_2$ (i.e. an oxygen content of less than 16%).

Preferably, said bacteria according to the present invention are cultivated in an air atmosphere.

The anaerobic bacteria can be either strict anaerobic bacteria or facultative anaerobic bacteria also called aerotolerant anaerobes, i.e. anaerobic bacteria that tolerate oxygen but do not need it to grow or aerobic bacteria that tolerate the absence of oxygen to grow.

Among the strict anaerobic bacteria, particular mention may be made of the other strict anaerobic bacteria belonging to the genera *Acidaminococcus, Alistipes, Anaerococcus, Anaerosalibacter, Amazonia, Atopobium, Bifidobacterium, Blautia, Bacteroides, Barneslella, Clostridium, Collinsella, Dielma, Eggerthella, Finegoldia, Flavonifractor, Fusobacterium, Gordombacter, Guyana, Holdemania, Odoribacter, Parabacteroides, Parvimonas, Prevotella, Peptostreptococcus, Peptoniphilus, Porphyromonas, Prevotella, Solobacterium, Tissierella, Turicibacter, Ruminococcus* and *Veillonella*.

Among the facultative anaerobic bacteria, particular mention may be made of other facultative anaerobic bacteria belonging to the genera *Actinomyces, Aerococcus, Aeromonas, Aneurinibacillus, Bacillus, Bartonella, Cedecea, Citrobacter, Corynebacterium, Derambacter, Eikenella, Enterobacter, Enterococcus, Escherichia, Eubacterium, Gardnerella, Gemella, Granulicatella, Hafnia, Haemophilus Kingella, Klebsellia, Lactobacillus, Lactococcus, Lysinibacillus, Morganella, Paenibacillus, Pasteurella, Pediococcus, Propionibacterium, Proteus, Providencia, Serratia, Raoultella, Rothia, Staphylococcus, Streptococcus* and *Weissella*.

Other features and advantages of this invention will become clearer by reading the detailed description that follows, which is illustrative and non-limiting.

FIG. 1 shows the comparison of the growth of anaerobic bacteria in the three media A, B and C tested in Example 3.

In order to compare the efficacy of the different culture media tested below, 10 anaerobic and 20 aerobic bacteria most commonly encountered in hospital routine were cultured using the reference methods (use of anaerobic bottles to cultivate anaerobic bacteria and aerobic bottles to cultivate aerobic bacteria). The list of these bacteria and their culture conditions are detailed in Table 1 below. These strains are in the laboratory's strain collection, the CSUR (Collection de Souches de l'Unité Rickettsies).

TABLE 1

List of microorganisms used in this study

| Aerobic bacteria | Anaerobic bacteria |
|---|---|
| *Staphylococcus aureus* P412 | *Bacteroides nordii* P3192 |
| *Enterobacter aerogenes* P455 | *Propionibacterium avidum* P3346 |
| *Escherichia coli* P430 | *Clostridum irreguiare* P1913 |
| *Klebsiella oxytoca* P1603 | *Clostridum massilioamazoniensis* P1360 |
| *Streptococcus agaiactiae* P4162 | *Clostridum butyricum* P344 |
| *Serratia marcescens* P587 | *Clostridum beijerinckii* P883 |
| *Enterococcus faecaiis* P2282 | *Bacteroides thetaiotaomicron* P575 |
| *Proteus mirabilis* P2711 | *Propionibacterium acnes* P637 |
| *Pseudomonas aeruginosa* P2378 | *Finegoidia magna* P588 |
| *Streptococcus mitis* P4157 | *Bacteroides fragilis* P444 |
| *Staphylococcus epidermidis* P4227 | *Akkermansia muciniphiia* P4531 and P3284 |
| *Morganella morganii* P4358 | *Prevoteiia histicoia* P1055 |
| *Citrobacter freundii* P4462 | *Prevoteiia denticoia* P1023 |
| *Enterobacter cloacae* P4822 | |
| *Bacillus circuians* P655 | |
| *Neisseria meninigitidis* P782 | |
| *Streptococcus pneumoniae* P3582 | |
| *Staphylococcus hominis* P3863 | |
| *Acinetobacter baumanii* P1976 | |
| *Haemophilus influenzae* P4027 | |

To test the growth of bacteria in different media, in aerobic atmosphere, the inventors emptied blood culture bottles and filled them with the culture medium. Once the mixture was homogeneous and the powders dissolved, the medium was filtered through a 0.2 μm thick filter to sterilize it. Forty millilitres of this medium was then transferred to each of the culture bottles, containing an aerobic atmosphere.

In order to inoculate the culture bottles with the bacteria, the inventors diluted for each bacteria a colony, which corresponds to about $10^6$ bacteria, in 1 millilitre of the same culture medium. After vortexing the tube containing this mixture, in order to properly dilute the colony in the liquid, the inventors injected the millilitre into the culture bottle using a syringe and sterile needle and incubated the bottle at 37° C. for 72 hours for anaerobic bacteria and 24 hours for aerobic bacteria. The same protocol was performed for each bacterium. One millilitre of medium containing $10^6$ bacteria having been introduced into a 40 millilitre culture bottle, the final quantity of bacteria in the culture bottle is $2.5 \times 10^4$ bacteria.

The aerobic bacteria used to carry out this study are cultivated and inoculated on Columbia agar+5% sheep blood agar medium incubated in an incubator maintained at a constant temperature of 37° C. without the addition of $CO_2$. Anaerobic bacteria were grown on the same medium and deposited in anaerobic jars equipped with anaerobic generators. After growth, aerobic and anaerobic bacteria were identified by MALDI-TOF mass spectrometry as described above [4].

The inventors studied the growth of the aerobic bacterial strains, and of the anaerobic bacterial strains, of Table 1, in 3 different liquid media.

To inoculate the bacteria into the blood culture bottles, the inventors prepared bacterial suspensions of each of the strains tested. For this purpose, 1 mL of each culture medium respectively was distributed into each Eppendorf tube, with three Eppendorf tubes per bacterium (one tube for each different medium).

For each bacterium, one colony, corresponding to approximately $10^6$ bacteria, was introduced into the Eppendorf tube containing 1 mL of culture medium. The inventors vortexed the tube in order to obtain a homogeneous mixture of the colony in the culture medium. They then inoculated the bacteria into the culture bottle using a syringe and a sterile needle.

The culture bottle was then incubated for 72 hours at 37° C.

This protocol was carried out for each of the bacteria and each of the media.

In FIG. 1, the results of the growth of anaerobic bacteria under aerobic conditions are reported. After 72 hours of incubation, the inventors measured the optical density (OD) of each culture bottle. To have an objective measurement, they made the control on uninoculated culture medium, in order to show bacterial growth.

The OD was measured for each of the bacteria in each of the media. For example, for the test medium, the control or zero was made with the same uninoculated medium, then the OD measurement was made for each of the bacteria. The control is always made with the medium that has been introduced into the culture whose OD is to be measured. The measuring device (Fisher scientific, Illkirch, France) does not measure ODs above 2, which correspond to strong bacterial growths.

Example 1

The inventors tested different antioxidants, as well as different mixtures and selected the mixture described above, in the formula of the culture medium according to the invention.

In order to select the best mixture of antioxidants, the inventors tested a total of 13 antioxidants.

First, the inventors tested the base mixture of antioxidants already known, namely sodium hydrosulphide ($Na_2S$), L-cysteine, ascorbic acid and glutathione, with peroxidase. Then, this same mixture with super oxide dismutase and finally with oxidase. However, the inventors did not observe any improvement in the growth of anaerobic bacteria under aerobic conditions.

They then tested 6 other antioxidants with the base mix described above. To do this, they experimented with 58 different combinations of all these antioxidants (see Tables 2A-2C below).

They tested these mixtures in a liquid medium, on 24-well culture plates (Greiner Bio-One International, Kremsmünster, Austria) with several aerobic and anaerobic bacteria including the bacterium *Finegoldia magna*, because it is the bacterium that had shown the most difficulty in growing during the tests carried out in the laboratory on the Versatrek™ medium with antioxidants.

For each plate, the inventors used three wells as a negative control, these wells contained 1 mL of the medium R-medium with the base antioxidants but without bacteria and three wells containing 1 mL of the same medium but with inoculation of the bacterium *Finegoldia magna* to show that there was not optimal growth of this bacteria in the initial mixture. In addition, to have a positive control, the inventors duplicated each plate and put the duplicate under anaerobic conditions, the bacteria tested being strict anaerobes.

In order to test each antioxidant and different combinations of these antioxidants, the inventors prepared stock solutions of the 6 antioxidants tested in addition to the base antioxidant mixture.

The medium R-medium with the base antioxidants was distributed into each well and to these wells, a certain volume of the stock solution of each antioxidant, corresponding to the desired concentration, was added to the wells. The distribution of antioxidants in the wells followed Table 2. The volume of R-medium with base antioxidants added to the wells is the difference between the 1 mL, desired as final volume and the volumes of added antioxidants. Indeed, to avoid creating bias, the inventors wanted the final volume, after the addition of antioxidants, in each well to be 1 mL The stock solutions of the 6 antioxidants were prepared in the following quantities and weight proportions:

Catalase: 100 mg of catalase was dissolved in 100 mL of distilled water. A stock solution at a concentration of 1 g/L was obtained. To obtain a final concentration in each well of 160 mg/L, 160 µL of the stock solution was added to the appropriate wells.

Ubiquinol: 100 mg of ubiquinol was dissolved in 100 mL of distilled water. A stock solution at a concentration of 1 g/L was obtained. To obtain a final concentration in each well of 160 mg/L, 160 µL of the stock solution was added to the appropriate wells.

BHT: 50 mg of BHT was dissolved in 10 mL of ethanol as BHT is not soluble in water. A stock solution at a concentration of 5 g/L was obtained. To obtain a final concentration of 100 mg/L in each well, 20 µL of the stock solution was added to the appropriate wells.

Vitamin E: 10 mg of vitamin E was dissolved in 10 mL of ethanol as vitamin E is not soluble in water. A stock solution at a concentration of 1 g/L was obtained. To obtain a final concentration in each well of 100 µM or 43 mg/L, 43 µL of the stock solution was added to the appropriate wells.

Lipoic Acid: 100 mg of lipoic acid was dissolved in 10 mL of ethanol as lipoic acid is not soluble in water. A stock solution at a concentration of 10 g/L was obtained. To obtain a final concentration in each well of 100 mg/L, 10 µL of the stock solution was added to the appropriate wells.

NAD: 10 mg of NAD was dissolved in 10 mL of distilled water. A stock solution at a concentration of 1 g/L was obtained. To obtain a final concentration of 15 mg/L in each well, 15 µL of the stock solution was added to the appropriate wells.

The inventors measured the pH of each stock solution and adjusted it to a pH of 7.3±0.2 when necessary.

The inventors prepared a suspension of the bacterium *Finegoldia magna* concentrated to $10^4$ and took 100 µL of this solution and introduced it into each of the wells, in order to obtain a final bacterial concentration of $10^3$ bacteria per millilitre. They then incubated the positive control dishes under anaerobic conditions and the test plates under aerobic conditions for 72 h at 37° C.

After 72 h of incubation, the inventors observed the plates and selected the combination of antioxidants that caused the greatest turbidity in the liquid medium. They did not quantitatively measure bacterial growth, they relied on an observation of a possible turbidity reflecting bacterial growth. Some other wells showed a slight turbidity but nothing comparable to the surprising turbidity of the selected most favourable combination of the 7 antioxidants in Table 2B with the addition of—catalase, ubiquinol and lipoic acid to the base mixture of antioxidants, already known, namely sodium hydrosulphide (Na$_2$S), L-cysteine, ascorbic acid and glutathione.

The most favourable combination for the growth of this bacterium was the base antioxidant mixture comprising antioxidants, sodium hydrosulphide (Na$_2$S), L-cysteine, ascorbic acid and glutathione, combined with the 3 additional antioxidants: ubiquinol, catalase and lipoic acid.

Tables 2A-2C: Combinations of the different antioxidants, with R-medium as the basal medium with the 4 base antioxidants (sodium hydrosulphide (Na$_2$S), L-cysteine, ascorbic acid, glutathione) (3 tables 2A, 2B and 2C, each table representing one plate).

In Tables 2A to 2C:

BHT=Butylhydroxytoluene

NAD=Nicotinamide adenine dinucleotide

BHT is a synthetic antioxidant, E321, listed as an antioxidant in the Codex Alimentarius. [5]).

NAD is an endogenous niacin coenzyme 1 A antioxidant found in every living mammalian cell.

TABLE 2A addition of 2 antioxidants

| Negative control | Negative control | Negative control | R-medium base without uric acid with F. magna | R-medium base without uric acid with F. magna | R-medium base without uric acid with F. magna |
|---|---|---|---|---|---|
| Catalase 160 mg/L | Ubiquinol 160 mg/L | BHT 100 mg/L | Vitamin E 100 µM or 43 mg/L | NAD 15 mg/L | Lipoic acid 10 mg/L |
| Catalase Ubiquinol | Catalase BHT | Catalase Vitamin E | Catalase NAD | Catalase Lipoic acid | Ubiquinol BHT |
| Ubiquinol Vitamin E | Ubiquinol NAD | Ubiquinol Lipoic acid | BHT Vitamin E | BHT NAD | BHT Lipoic acid |

TABLE 2B addition of 3 or 4 antioxidants

| Negative control | Negative control | Negative control | R-medium base without uric acid with F. magna | R-medium base without uric acid with F. magna | R-medium base without uric acid with F. magna |
|---|---|---|---|---|---|
| Vitamin E NAD BHT | Vitamin E Lipoic acid NAD | Catalase Ubiquinol BHT | Catalase Ubiquinol Vitamin E | Catalase Ubiquinol NAD | Catalase Ubiquinol Lipoic acid |
| Ubiquinol BHT Vitamin E | Ubiquinol BHT NAD | Ubiquinol BHT Lipoic acid | Ubiquinol Vitamin E NAD | Ubiquinol Vitamin E Lipoic acid | Ubiquinol NAD Lipoic acid |
| Catalase Ubiquinol Lipoic acid BHT | Catalase BHT Vitamin E NAD | Catalase BHT Vitamin E Lipoic acid | Catalase Vitamin E NAD Lipoic acid | Ubiquinol BHT Vitamin E NAD | Ubiquinol BHT Vitamin E Lipoic acid |

TABLE 2C addition of 5 antioxidants

| Negative control | Negative control | Negative control | R-medium base without uric acid with F. magna | R-medium base without uric acid with F. magna | R-medium base without uric acid with F. magna |
|---|---|---|---|---|---|
| Ubiquinol BHT NAD Lipoic acid | Ubiquinol Vitamin E NAD Lipoic acid | BHT Vitamin E NAD Lipoic acid | Catalase Ubiquinol BHT Vitamin E | Catalase Ubiquinol BHT Vitamin E Lipoic acid | Catalase Ubiquinol BHT NAD Lipoic acid |
| Catalase Ubiquinol NAD Lipoic acid Vitamin E | Catalase Vitamin E BHT NADLipoic acid | Ubiquinol Vitamin E BHT NAD Lipoic acid | NAD Lipoic acid Catalase Ubiquinol Vitamin E BHT | | |

Example 2

In order to demonstrate that this better growth of the anaerobic bacteria tested, under aerobic conditions, was due solely to the mixture of antioxidants and not to the basal culture medium used, the inventors tested the old version of antioxidants (sodium hydrosulphide (Na$_2$S)), L-cysteine, ascorbic acid, glutathione) in the marketed medium Versatrek™ (i2a, Montpelier, France) and the new version of antioxidants in the same medium (sodium hydrosulphide (Na$_2$S), L-cysteine, ascorbic acid, glutathione, catalase, ubiquinol and lipoic acid.

Concerning the Versatrek™ medium+4 antioxidants of the prior art, the supplemented VersaTREK™ bottles (i2a, Montpellier, France) were supplemented with the following conventional antioxidant compounds in the following quantities and weight proportions per 25 mL:

Sodium hydrosulphide (Na$_2$S): 0.25 g (0.025%)
Uric acid: 0.2 g (0.02%)
Ascorbic acid: 0.5 g (0.05%)
Glutathione: 0.05 g (0.005%)

Concerning the Versatrek medium+7 antioxidants according to the invention, the supplemented VersaTREK™ bottles (i2a, Montpelier, France) were supplemented with the following conventional antioxidant compounds in the following quantities and weight proportions per 1 L:

Sodium hydrosulphide (Na$_2$S): 0.5 g (0.05%)
Uric acid: 0.4 g (0.04%)
Ascorbic acid: 1 g (0.1%)
Glutathione: 0.1 g (0.01%)
Catalase: 0.16 g (0.016%)
Ubiquinol: 0.16 g (0.016%)
Lipoic acid: 0.010 g (0.001%)

The aforementioned anaerobic bacteria were tested in these two media and incubated at 37° C. for 72 hours and the inventors observed a better growth of these bacteria in the Versatrek medium+7 antioxidants mixture.

The inventors were able to deduce that the basal nutritional medium used does not matter, if the mixture of the 7 antioxidants is added to the medium, the anaerobic bacteria will grow better under aerobic conditions.

Example 3: Comparative Tests on the Growth of Common Fastidious Anaerobic Bacteria The growth performance of the different culture media in culture incubated in an incubator at 37° C. is evaluated below, namely the universal culture bottle medium according to the present invention and known comparative media comprising a conventional aerobic and anaerobic culture medium BD BACTEC™ based on enriched trypticase soy broth (medium A in FIG. 1) and a VersaTREK™ blood culture bottle medium supplemented with the antioxidants described below (medium B in FIG. 1) (item number 191401, VersaTREK REDOX 1 aerobic from i2a, Montpelier, France) [3].

The culture medium according to the invention named "R medium" (medium C in FIG. 1) comprises the following components in the following quantities and weight proportions per 1 L:

Basal Medium:
  Casein hydrolysate: 15 g (1.5%)
  Proteose peptone: 15 g (1.5%)
  Yeast extract: 10 g (1%)
  α-Ketoglutarate: 2 g (0.2%)
  Sodium chloride (NaCl): 5 g (0.5%)
  Glucose: 10 g (1%)
  Dipotassium phosphate ($K_2HPO_4$): 0.83 g (0.083%)

Antioxidant Compounds:
  Sodium hydrosulphide ($Na_2S$): 0.5 g (0.05%)
  L-Cysteine: 0.5 g (0.05%)
  Ascorbic acid: 1 g (0.1%)
  Glutathione: 0.1 g (0.01%)
  Catalase: 0.16 g (0.016%)
  Ubiquinol: 0.16 g (0.016%)
  Lipoic acid: 0.010 g (0.001%)

The other two media tested, namely the BD BACTEC™ anaerobic culture bottles and the supplemented VersaTREK™ bottles (i2a, Montpellier, France) supplemented with the following conventional antioxidant compounds in the following quantities and weight proportions per 25 mL:
  Sodium hydrosulphide ($Na_2S$): 0.25 g (0.025%)
  Uric acid: 0.2 g (0.02%)
  Ascorbic acid: 0.5 g (0.05%)
  Glutathione: 0.05 g (0.005%)

The results showed that for the same incubation time, the OD measured for the anaerobic bacteria incubated in aerobic atmosphere is higher with the culture medium of the present invention (medium C in FIG. 1), compared with the antioxidant supplemented VersaTREK™ media (medium B in FIG. 1), and the culture bottle with the anaerobic culture medium BD BACTEC™ (medium A in FIG. 1), commonly used as shown in FIG. 1.

FIG. 1 represents the ODs illustrating the growth of anaerobic bacteria in the three media A, B and C tested at 72 h incubation at 37° C. for the following 10 fastidious anaerobic bacteria commonly encountered in hospital practices: *Bacteroides nordii, Propionibacterium avidum, Clostridium irregular, Clostridium massilioamazoniensis, Clostridium butyricum, Clostridium beijerinckii, Bacteroides thetaiotaomicron, Propionibacterium acnes, Finegoldia magna* and *Bacteroides fragilis*.

Similar results were obtained for aerobic bacteria in the three media tested.

Example 4: Test for the Growth of Various Other Fastidious Bacteria Found in Humans in the Oral Cavity or Gastrointestinal Tract The culture medium of the present invention R medium and the supplemented Versatek™ medium remain identical to those described in Example 3.

The inventors tested 2 strains of *Prevotella: P. denticola* and *P. histicola* and 2 strains of *Akkermansia muciniphila* P3284 and P4531.

These bacteria are strict anaerobes and are found in humans in the oral cavity or the gastrointestinal tract.

In the same way as described above, the inventors prepared bacterial suspensions of each of the strains tested. For this purpose, 1 mL of culture medium was distributed into each Eppendorf tube, with one Eppendorf tube per bacterium.

For each bacterium, one colony, corresponding to approximately $10^6$ bacteria, was introduced into the Eppendorf tube containing 1 mL of culture medium. The inventors vortexed the tube in order to obtain a homogeneous mixture of the colony in the culture medium. They then inoculated the bacteria into the blood culture bottle using a syringe and a sterile needle.

The culture bottle was then incubated for 5 days at 37° C.

The 4 strains of the 3 bacteria grew in the medium according to the invention R-medium and did not grow in the supplemented Versatek™ medium described in Example 3.

BIBLIOGRAPHY (1) Strobel H. Basic laboratory culture methods for anaerobic bacteria. In: Jonathan R. Mielenz, editor. 2009 p 247-248

(2) N. Dione, S. Khelaifia, B. La Scola, J. C. Lagier, D. Raoult. A quasi-universal medium to break the aerobic/anaerobic bacterial culture dichotomy in clinical microbiology. G. Greub, editor. Clin Microbiol Infect. 2016 January; 22(1):53-8. January 2016.

(3) Grégory Dubourg, Elodie Guilhot, Saber Khelaifia, Enora Tomei, Jean-Paul Casalta, Pierre-Yves Lévy, Hervé Tissot-Dupont, Didier Raoult. Evaluation of the Versatrek universal vial in the diagnosis of bacteremia: a preliminary report. (submitted).

(4) Seng P, Drancourt M, Gouriet F, La Scola B, Fournier P E, Rolain J M, Raoult D. Ongoing revolution in bacteriology: routine identification of bacteria by matrix-assisted laser desorption ionization time-of-flight mass spectrometry. Clin Infect Dis. 2009 Aug. 15; 49(4):543-51.

(5) Codex Alimentarius, International Food Standards. CAC/GL 36-1989. Page 10

The invention claimed is:

1. A polyvalent liquid culture medium for culture in aerobic atmosphere of anaerobic bacteria or aerobic bacteria comprising:
  a basal culture medium for aerobic and anaerobic bacteria;
  wherein the basal culture medium comprises a mixture of the following antioxidant compounds: sodium hydrosulphide ($Na_2S$), L-cysteine, ascorbic acid, glutathione, catalase, ubiquinol and lipoic acid.

2. The culture medium according to claim 1, wherein said antioxidant compounds comprise the following quantities and weight proportions per 1 L:
  sodium hydrosulphide: at least 0.25 g (0.025%);
  L-cysteine: at least 0.25 g (0.025%);
  ascorbic acid: at least 0.5 g (0.05%);
  glutathione: at least 0.1 g (0.01%);
  catalase: at least 0.06 g (0.006%);
  ubiquinol: at least 0.06 g (0.006%); and
  lipoic acid: at least 0.01 g (0.001%).

3. The culture medium according to claim 1, further comprising the following nutrient components in said basal culture medium:
- a source of carbon and nitrogen selected from the group consisting of a yeast extract, an acetate salt, and a tryptic peptone,
- a source of phosphorus,
- at least one sugar,
- at least one salt of metals selected from K, Mg, Na, and Ca,
- at least one pH-regulating buffer substance for adjusting the pH from 7 to 8, or $NaHCO_3$ for adjusting the pH to 7.5, and
- at least one vitamin or growth factor.

4. The culture medium according to claim 1, wherein said basal culture medium is a conventional acellular bacterial medium comprising components selected from an extract of ground material, or lysate of multicellular tissue, an enzyme digestate, soybean and/or animal tissue, a peptone, a yeast extract, a sugar, a NaCl and/or $Na_2PO_4$ salt.

5. The culture medium according to claim 1, wherein said basal culture medium is a liquid culture medium for culturing anaerobic bacteria in a blood, stool, sputum, or vaginal secretion sample.

6. The culture medium according to claim 1, wherein said basal culture medium comprises the following nutrient components:
- casein hydrolysate;
- proteose peptone;
- yeast extract;
- glucose;
- sodium chloride (NaCl); and
- a growth factor: α-ketoglutarate.

7. The culture medium according to claim 6, comprising the following components in the following quantities and weight proportions per 1 L:
- casein hydrolysate: 15 g (1.5%),
- proteose peptone: 15 g (1.5%),
- yeast extract: 10 g (1%),
- α-ketoglutarate: 2 g (0.2%),
- sodium chloride (NaCl): 5 g (0.5%),
- glucose: 10 g (1%),
- dipotassium phosphate ($K_2HPO_4$): 0.83 g (0.083%),
- sodium hydrosulphide ($Na_2S$): 0.5 g (0.05%),
- L-cysteine: 0.5 g (0.05%),
- ascorbic acid: 1 g (0.1%),
- glutathione: 0.1 g (0.01%),
- catalase: 0.16 g (0.016%),
- ubiquinol: 0.16 g (0.016%),
- lipoic acid: 0.010 g (0.001%), wherein the pH of the solution is adjusted to 7.5±0.2 with 10 M KOH.

8. A process for the in vitro culture of an aerobic or anaerobic bacterium under aerobic atmosphere with a culture medium as claimed in claim 1.

9. The process according to claim 8, wherein said bacterium is cultured in a blood, stool, sputum, or vaginal secretion sample.

10. The process according to claim 8, wherein said anaerobic bacterium is selected from the group consisting of *Akkermansia muciniphila, Bacteroides fragilis, Bacteroides nordii, Bacteroides thetaiotaomicron, Clostridium beijerinckii, Clostridium butyricum, Clostridium massilioamazoniensis, Clostridium irregulare, Finegoldia magna, Propionibacterium acnes, Propionibacterium avidum, Prevotella denticola*, and *Prevotella histicola*.

11. The culture medium according to claim 1, wherein said antioxidant compounds comprise the following quantities and weight proportions per 1 L:
- sodium hydrosulphide: from 0.25 g to 0.5 g (0.025 to 0.05%);
- L-cysteine: from 0.25 g to 0.5 g (0.025 to 0.05%);
- ascorbic acid: from 0.5 to 1 g (0.05 to 0.1%);
- glutathione: from 0.1 to 0.5 g (0.01 to 0.05%);
- catalase: from 0.06 to 0.16 g (0.006 to 0.016%);
- ubiquinol: from 0.06 to 0.16 g (0.006 to 0.016%); and
- lipoic acid: from 0.01 to 0.015 g (0.001 to 0.0015%).

12. The culture medium according to claim 3, wherein the at least one salt is NaCl.

13. The culture medium according to claim 3, wherein the at least one pH-regulating buffer substance for adjusting the pH from 7 to 8 is $K_2HPO_4$.

14. The culture medium according to claim 4, wherein the enzyme digestate is an enzyme digestate of casein.

15. The culture medium according to claim 4, wherein the sugar is dextrose or glucose.

* * * * *